(12) United States Patent
Kastelein

(10) Patent No.: US 7,537,570 B2
(45) Date of Patent: May 26, 2009

(54) AUTOMATED MAPPING OF ANATOMICAL FEATURES OF HEART CHAMBERS

(75) Inventor: Nathan Kastelein, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 11/853,507

(22) Filed: Sep. 11, 2007

(65) Prior Publication Data

US 2008/0064969 A1    Mar. 13, 2008

Related U.S. Application Data

(60) Provisional application No. 60/843,637, filed on Sep. 11, 2006.

(51) Int. Cl.
*A61B 5/02* (2006.01)
(52) U.S. Cl. .................................. 600/508
(58) Field of Classification Search .......... 600/508; 607/119, 122
See application file for complete search history.

(56) References Cited

U.S. PATENT DOCUMENTS

| | | | | |
|---|---|---|---|---|
| 4,955,382 A * | 9/1990 | Franz et al. | | 600/375 |
| 5,423,878 A * | 6/1995 | Franz | | 607/122 |
| 5,654,864 A | 8/1997 | Ritter et al. | | |
| 5,931,818 A | 8/1999 | Werp et al. | | |
| 6,014,580 A | 1/2000 | Blume et al. | | |
| 6,015,414 A | 1/2000 | Werp et al. | | |
| 6,063,078 A * | 5/2000 | Wittkampf | | 606/41 |
| 6,128,174 A | 10/2000 | Ritter et al. | | |
| 6,148,823 A | 11/2000 | Hastings | | |
| 6,152,933 A | 11/2000 | Werp et al. | | |
| 6,157,853 A | 12/2000 | Blume et al. | | |
| 6,185,464 B1 * | 2/2001 | Bonner et al. | | 607/119 |
| 6,212,419 B1 | 4/2001 | Blume et al. | | |
| 6,241,671 B1 | 6/2001 | Ritter et al. | | |
| 6,287,301 B1 * | 9/2001 | Thompson et al. | | 606/33 |
| 6,292,678 B1 | 9/2001 | Hall et al. | | |

(Continued)

OTHER PUBLICATIONS

International Search Report and Written Opinion for corresonding PCT/US07/78147 Date: Aug. 25, 2008 pp. 8.

*Primary Examiner*—George Manuel
*Assistant Examiner*—Christopher A Flory
(74) *Attorney, Agent, or Firm*—Harness, Dickey & Pierce, P.L.C.

(57) ABSTRACT

A method is provided to facilitate the movement of a medical device for automated mapping of anatomical surfaces of a subject's heart with a remote navigation. The method may include one or more distinct movements for moving a medical device for mapping a portion of an anatomical surface of a subject's heart. Upon establishing contact of the tip of the medical device with a surface of the heart, one method provides for moving the medical device along the surface of the heart towards an anatomical feature until a loss of contact with the surface is sensed, and determining the point where the loss of contact occurred to identify at least one point along the anatomical feature. The process may be repeated to identify a multiplicity of points that serve to define the ridge on the interior heart surface. The ridge location in the anatomical map can be used as a reference or guide to facilitate the further mapping of physiological properties and to plan therapy delivery during the medical procedure.

24 Claims, 1 Drawing Sheet

U.S. PATENT DOCUMENTS

| | | |
|---|---|---|
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,468,265 B1* | 10/2002 | Evans et al. .................... 606/1 |
| 6,468,271 B1* | 10/2002 | Wentzel et al. ................ 606/34 |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al. |
| 7,248,914 B2 | 7/2007 | Hastings et al. |
| 7,264,584 B2 | 9/2007 | Ritter et al. |
| 2001/0038683 A1 | 11/2001 | Ritter et al. |
| 2001/0041891 A1* | 11/2001 | Thompson et al. ............. 606/41 |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0055410 A1* | 3/2003 | Evans et al. .................... 606/1 |
| 2003/0125752 A1 | 7/2003 | Werp et al. |
| 2003/0208252 A1* | 11/2003 | O'Boyle et al. ............. 607/122 |
| 2004/0006301 A1 | 1/2004 | Sell et al. |
| 2004/0006333 A1* | 1/2004 | Arnold et al. ................. 606/15 |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0147864 A1* | 7/2004 | Lenker et al. ............. 604/4.01 |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0038419 A9* | 2/2005 | Arnold et al. ................. 606/15 |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0107808 A1* | 5/2005 | Evans et al. ................. 606/139 |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr., et al. |
| 2005/0182315 A1 | 8/2005 | Ritter et al. |
| 2005/0256398 A1 | 11/2005 | Hastings et al. |
| 2005/0273006 A1* | 12/2005 | Stewart et al. ............... 600/433 |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025675 A1 | 2/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0276775 A1* | 12/2006 | Rosenberg et al. ............. 606/1 |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |

| | | | | | |
|---|---|---|---|---|---|
| 2007/0073288 A1 | 3/2007 | Hall et al. | 2007/0179492 A1 | 8/2007 | Pappone |
| 2007/0088197 A1 | 4/2007 | Garibaldi et al. | 2007/0197899 A1 | 8/2007 | Ritter et al. |
| 2007/0135804 A1 | 6/2007 | Ritter | 2007/0197901 A1 | 8/2007 | Viswanathan |
| 2007/0137656 A1 | 6/2007 | Viswanathan | 2007/0197906 A1 | 8/2007 | Ritter |
| 2007/0146106 A1 | 6/2007 | Creighton, IV | 2007/0225589 A1 | 9/2007 | Viswanathan |
| 2007/0149946 A1 | 6/2007 | Viswanathan | 2008/0161668 A1* | 7/2008 | Wittkampf et al. .......... 600/372 |
| 2007/0161882 A1 | 7/2007 | Pappone | 2008/0172049 A1* | 7/2008 | Bredno et al. ................. 606/29 |
| 2007/0167720 A1 | 7/2007 | Viswanathan | | | |

* cited by examiner

AUTOMATED MAPPING OF ANATOMICAL FEATURES OF HEART CHAMBERS

CROSS-REFERENCE TO RELATED APPLICATION

This application claims priority to prior U.S. Patent Application Ser. No. 60/843,637, filed Sep. 11, 2006, the entire disclosure of which is incorporated herein by reference.

BACKGROUND

This invention relates to automated mapping of heart tissue surfaces, and in particular to the mapping of various anatomical regions of the heart having differing geometry such as local ridges.

The mapping process is carried out by a medical device that is driven or controlled by a remote navigation system. Various features of the invention provide for an efficient method of automation of the mapping process. Besides the geometry of the anatomy, electrical or other physiological information can also be collected during the mapping process.

SUMMARY

Some embodiments of the method of this invention provide for automatically or semi-automatically mapping an anatomical surface of a subject's heart with the help of a remote navigation system. One example of such a system is the Stereotaxis' Niobe magnetic navigation system, while mechanically actuated or electrostrictively actuated remote navigation schemes are other possibilities. The embodiments provide a method for advancing a medical device within a subject's body near to at least one known anatomical feature of the heart, establishing contact with the surface of the heart, and moving the medical device until a loss of contact is detected, to identify at least one point along the known anatomical feature. The various embodiments of a method for locating at least one point on a ridge of a subject's heart provide for a more accurate map of the anatomy and electrical activity, which can then be used to deliver therapy such as Radio Frequency ablation.

Thus, methods in accordance with the preferred embodiments of the present invention facilitate the mapping of anatomical features of a subject's heart. These and other features and advantages will be in part apparent and in part pointed out hereinafter.

DETAILED DESCRIPTION

Figure 1:
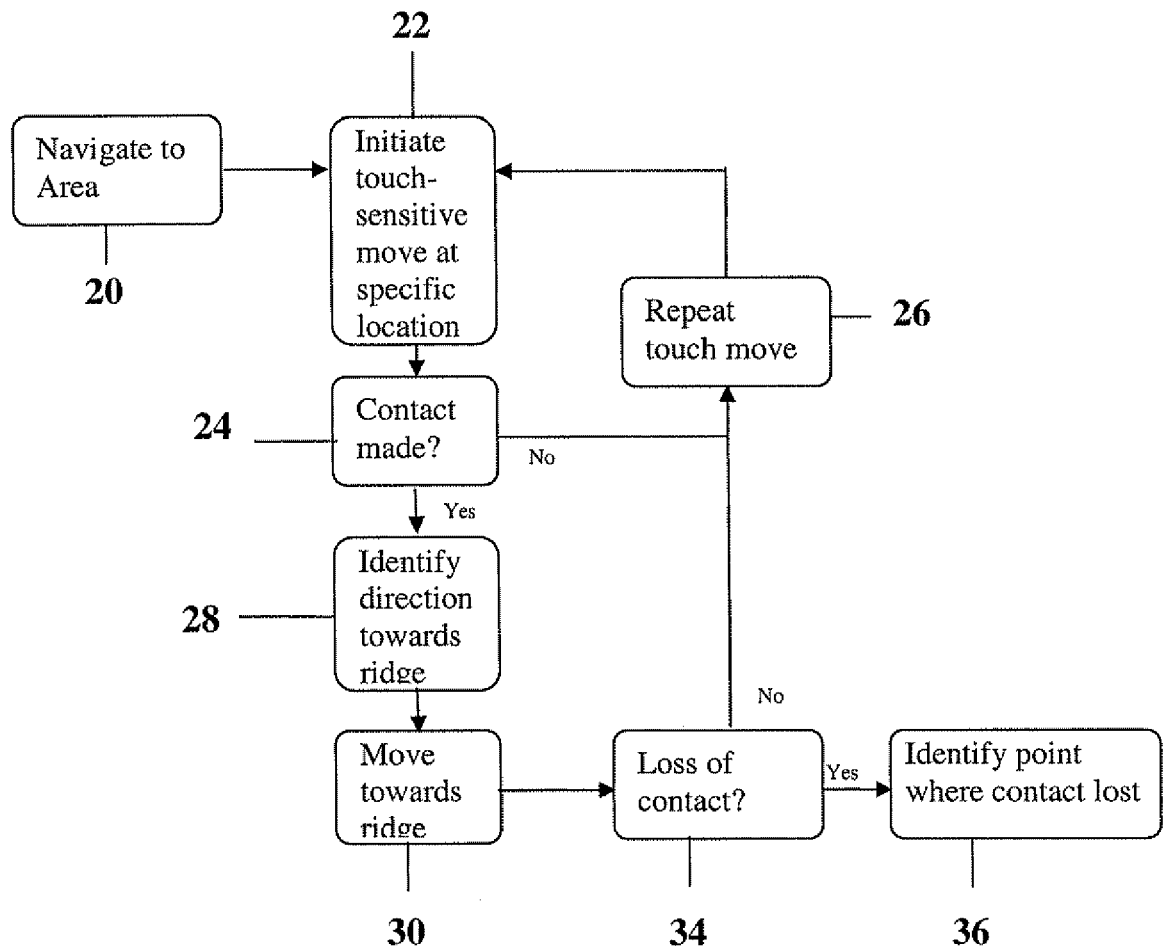
FIG. 1 is a flow chart illustrating the method of mapping a ridge along a subject's heart to identify the location of the ridge.

The methods of the preferred embodiments of this invention facilitate the automated movement of a medical device for mapping an anatomical surface of a subject's heart, and also for electrically mapping a portion of a heart (which could be either an atrium or a ventricle) to identify abnormalities in electrical signal propagation. Once such abnormalities have been identified, therapy such as intracardiac Radio Frequency (RF) ablation may be delivered using the geometrical and electrical information provided by the map.

The methods of the preferred embodiments involve the use of one or more sequenced movements for moving a medical device for mapping a portion of an anatomical surface of a subject's heart. The physician directs the medical device or catheter to a location in a cardiac chamber, where the catheter may be used to "map" the surface of at least a portion of a subject's heart. The method may record the location of one or more points where the catheter makes contract with the anatomical surface during the movement of the catheter across the tissue surface. The medical device may further "map" the electrical impulses across the surface area of the heart.

The method of this preferred embodiment can be advantageously conducted with a remote navigation system, and in particular an automated remote navigation system such as for example an automated magnetic navigation system, available from Stereotaxis, Inc., St. Louis, Mo. Such an automated system can move the catheter to each of a plurality of locations in a preplanned pattern, such as a grid or a spiral. Such a system could also be programmed to selected locations intelligently, for example avoiding locations where the tissue can be predicted to be unviable based on locations where the tissue has already been determined to be unviable.

In one aspect of the present disclosure, one or more catheter movements may be employed for moving a catheter across an anatomical surface to map the surface. Such movements may include a touch sensitive move to establish contact with the tissue at a select location, and moving the catheter to establish a pattern having a reasonably distributed set of points for a given region of the heart, where the pattern and points are unique to a specific region of the heart. The navigational system would control the catheter movement to maintain or almost always maintain contact of the catheter against the tissue surface area being mapped. In the case of a subject's heart, broad areas like the right ventricle region of the heart include sweeps, while other areas like the right or left auricle/atrium may include deflections and minor movements. There are at least nine regions consistent with the anatomy of the heart, in which distinct catheter movements or patterns are utilized.

While the examples presented below discuss a preferred embodiment in the form of a magnetic navigation system, the methods are general and other remote navigation methods such as a mechanically actuated system can be employed as would be obvious to those skilled in the art. The examples and navigation actuation method given here are provided for purposes of non-limiting illustration only. Examples of distinct catheter movements include advancing or retracting the catheter to a desired length or absolute distance, advancing or retracting the catheter a relative amount (in millimeters), advancing the catheter until a deflection of the tip of the catheter occurs, setting a magnetic field to a known orientation, adjusting the magnetic field until a deflection of the tip of the catheter occurs, retracting the catheter while the tip is deflected or contact is maintained with a tissue surface, and setting a retraction limit.

The command for "setting the retraction limit" prevents the catheter from retracting too far, and is a safety measure to insure that the catheter is not inadvertently withdrawn from the chamber through the transeptal puncture during automated movements.

Moving the catheter to an absolute length involves advancing or retracting the catheter to an absolute distance base on a calibrated Catheter Advancer System (CAS) length. This command can be used at the start of a series of movements to insure that the movement pattern is starting from a known position.

Moving the catheter a relative amount advances or retracts the catheter from the current position a specified number of millimeters. This command can be useful for implementing drag operations and can be combined with field changes to create a back and forth sweeping or aggregate motion.

The command for "setting the field direction" changes the magnetic field to a specified direction. This command is useful at the beginning of a series of motions to ensure pattern movements are started from a known tip direction.

One touch-sensitive movement entails a command for advancing the CAS until the tip is deflected, which movement causes the catheter to be advanced to the point at which the tip of the catheter contacts a tissue surface and is deflected by a minimum amount. As a safety measure, this command movement will not exceed a specified maximum distance. By iteratively advancing until contact and deflection occurs, this movement enables set-up of pattern movements to accommodate different chamber sizes and geometries. The command is also useful for additional discrete movements. Contact of the catheter with the heart wall can be sensed as described in Pending U.S. patent application Ser. No. 11/184,557 titled "Method of and Apparatus for Controlling Medical Navigation Systems".

Another touch-sensitive movement entails a command for adjusting the field direction to deflect the tip until contact is established, which movement changes the direction of the applied magnetic field to cause the tip to orient with the field or deflect until the tip is obstructed by a tissue surface. The field is changed in the direction specified by the user. Similar to the "advance until deflection" command, the field is changed until contact is established or the catheter deflection exceeds a predetermined threshold. This movement capability enables set-up of pattern movements to allow for some accommodation to chamber size and geometry. This command is useful in preparing "drag" pattern movements, and for "spoke" pattern touch sequences.

The command for "dragging while verifying contact" provides for retracting the catheter by a specified amount, while moving the catheter along a prescribed line. The drag operation is terminated if the tip deflection measurement falls below a specified minimum level, indicative of a loss of contact. This movement allows a drag line to be followed, but ends the motion early if contact is not being maintained. This movement is useful for large smooth surface areas of a chamber, and allows for collection of many points quickly.

The mapping of each region may comprise subsets of these and other exemplary catheter movements to create of distinct set of movements unique to a specific region of the heart. As an example, in the Left Atrium, there are at least nine regions of the heart having a distinct set of movements, which are: Posterior, Anterior, Inferior, Right Inferior, Right Anterior, Right Posterior, Left side, Left Atrial Appendage or Pulmonary Vein Ridge. The movements associated with each of these areas are described below.

Left Atrium

Posterior

The medical device or catheter is extended to the left atrial roof region, where a touch sensitive movement allows the working catheter length to be established. The catheter is advanced to deflect the tip to the posterior, and dragged across the wall while maintaining constant contact. Because the posterior part of the LA is slightly convex and relatively smooth, broad sweeping movements of the catheter are made from left to right and back while withdrawing the catheter slowly with the Computer Advancing System. This creates a wide zigzag type pattern that effectively covers the posterior aspect of the chamber.

Anterior

The anterior aspect of the chamber is similar to the posterior in that the working length is established by touching the roof and then deflecting the tip in an anterior direction. The movement vectors are kept from being too left lateral so as to avoid moving the catheter across the mitral valve.

Inferior

The catheter is advanced into the mid chamber region and then deflected inferiorly in a series of movements where the catheter is advanced and progressively directed more inferior. This move allows us to get the base of the chamber and near the septal region. The catheter is then moved from posterior to anterior while being retracted, thus sweeping out the floor of the chamber.

Right Inferior

Right inferior is a challenge because of the proximity to the transeptal puncture. The catheter is advanced to touch the atrial roof directly above the transeptal puncture; this sets a good right sided working distance of the catheter. The catheter is withdrawn a small amount to get freedom of movement and then oriented to strongly deflect the tip against the surface and towards the right side. A series of circular movements from anterior to posterior are made, where the CAS allows the catheter length to vary through out the movement, allowing this region to be identified.

Right Anterior

Right anterior is obtained by touching the atrial roof directly above the transeptal deflecting anteriorly and then dragging the catheter back while moving the catheter slightly from left to right and back.

Right Posterior

Right posterior is obtained by touching the atrial roof directly above the transeptal deflecting posteriorly and then dragging the catheter back while moving the catheter slightly from left to right and back.

Left Side

Left side moves are started by touching the atrial roof on the left side to set the working length of the catheter. The catheter is deflected anteriorly and posteriorly with varying degrees of inferior and superior deflection added. This allows for a series of touches to occur all over the left side. Because the catheter working length is long, these touching movements are more effective. The catheter is withdrawn slightly and the movements are repeated.

Left Atrial Appendage/Pulmonary Vein Ridge

The LAA/PV ridge is a challenging structure to identify due both to the structure's shape and the variability among patients. The strategy is to use a special touch sensitive movement that senses when contact is lost. The catheter is advanced in the direction of the LAA roof and a touch sensitive move sets the length. The catheter is then deflected posteriorly and dragged back until contact is lost as the catheter falls over the ridge. The catheter is advanced toward the pulmonary veins and deflected anteriorly back toward the LAA. Again the catheter is retracted slowly until contact is lost due to falling over the ridge. This sequence is repeated a few times at positions that are progressively more inferior.

The mapping process for finding an anatomical ridge is outlined in FIG. 1 with the flowchart provided therein. In step 20, the user or the remote navigation system navigates the medical device to the vicinity of the area of interest. In step 22, the device is advanced or other suitable movement actuated until it makes contact with the tissue surface as determined in step 24. In step 28, a direction of movement towards the ridge is identified (this could be pre-defined or it could be defined by the user), and in step 30 movement towards the ridge is executed. In step 34, if the device "slips off" the surface and loses contact, this is detected. The location of the device tip at which contact was lost is identified and recorded in step 36.

The unique aspects of this mapping capability involves using touch sensitive movements to establish contact at specific anatomical positions, and setting a working catheter length, to provide for flexibility to adapt combinations of movements to form patterns for different chamber sizes in individual patients. The combination of movements establishes a pattern of movement on a smooth wall, a pattern of movement over tendons, or a pattern of movement over ridged or trabeculated surfaces. Movement patterns also include avoidance of valves or other catheters. In one combination of movements, the movements define a ridge-finding pattern based on detecting a fall-off in contact. Another combination of movements creates a spiral pattern that identifies vein definition. Yet another combination of movements includes applying a magnetic field for deflecting the tip to establish and maintain contact of the tip with the tissue surface while advancing or retracting the catheter tip. Such movements can maintain the tip in contact with the tissue, and provide display verifying the contact, regardless of whether there is no discernable ECG signal or the tissue area is non-viable. The use of a magnetic field to establish contact also causes less wall distension. The series of movements in each section may comprise about 10-12 moves. The medical device or catheter may also be paused for 1.2 seconds at each position, or more generally between 0.5 and 5 seconds. Alternatively the localization/Electrophysiology mapping system may allow the user to decide when to move the catheter next.

Accordingly, a method for mapping at least one distinct anatomical surface comprises using touch sensitive movements to establish contact at specific anatomical positions, and setting a working catheter length, to provide for flexibility to adapt a combination of movements to form a pattern of continuous contact along the tissue surface. A combination of movements may comprise, for example, retracting the catheter while changing the field direction to move the tip back and forth to form a sweeping serpentine pattern, advancing or retracting the catheter while changing the field direction to move the tip to form a spiral pattern, or changing the field to deflect the tip until contact with the tissue surface is established and retracting the catheter until the tip loses contact with the tissue surface. The navigation system records the location of one or more points that the catheter has contacted during the combination of movements, which may be used to generate a surface rendering or to register a pre-operative image of the surface. The catheter may also be used to record sensed physiological data at a plurality of points on the tissue surface during the at least one select combination of movements, to map the electrical characteristics of the surface region of the heart.

In another aspect of the present disclosure, various embodiments of a method for locating at least one point on a ridge of a subject's heart are provided, for effecting registration with a pre-operative image of the heart. In one embodiment, the method comprises advancing a medical device within a subject's body near to at least one known anatomical feature of the heart, establishing contact with the surface of the heart, and moving the medical device until a loss of contact is detected, to identify at least one point along the known anatomical feature.

In an interventional medical system for directing and manipulating the distal tip of a medical device within a subjects body using a navigational system, the navigation system's coordinates are preferably registered to an imaging system's coordinates. One such navigation system that employs external magnetic fields to guide the medical device is the Niobe/Navigant system manufactured by Stereotaxis. In such a system, the magnet system is mechanically registered to the X-ray imaging system.

In minimally invasive medical procedures such as cardiac catheterizations, it is often important to be able to register a pre-operative image data set of portions of the heart to the imaging system. The navigation system, or alternatively a device localization system, can use a transformation matrix that will obtain a "registration" of the pre-operative image to the coordinates in the frame of reference of the imaging system. This involves initially obtaining three-dimensional anatomical data of a particular area of a subject's heart, such as for example the left atrial ridge.

The navigational system, or alternatively a device localization system, may utilize a method for locating points on the ridge using the medical device tip. Similar points on the surface of the corresponding three-dimensional pre-operative image of the heart portion may be used to find a suitable transformation matrix that effects a registration between the pre-operative image data and the actual ridge points shown in the X-ray imaging display. This registration will allow for overlay of a visual representation of the pre-operative image of the heart onto the X-ray image plane, which can serve as a visual aid in surgical navigation of a medical device within a subject's body.

In one embodiment of a method for locating at least one point on a ridge of a subject's heart for effecting registration, the method comprises advancing a medical device within a subject's body to the point near the surface of the subject's heart. The method then applies a magnetic field to al least one magnetically responsive element in the tip of the medical device to cause the tip to deflect (towards the heart) and establish contact with the surface of the heart. The method proceeds by retracting the medical device (gradually) while the tip is deflected against the surface of the heart, and detecting a variable change indicative of a loss of contact between the tip and heart surface along the ridge. Upon detecting such a variable change, the method determines the location of the tip at the point where a loss of contact occurred, to identify at least one point along a known anatomical surface for effecting registration of a pre-operative image of the heart.

In one embodiment, detecting a variable change comprises detecting a change in tip deflection of more than about 0.50 millimeters. In other method embodiments, the detection of the variable change may comprise continually measuring the value of the tip deflection and determining when a measured deflection value has changed from a previously measured value by more than a predetermined percentage. In still other method embodiments, the detection of the variable change may comprise detecting a variable change comprises detecting a decrease in contact force (which can be estimated as described in Pending U.S. patent application Ser. No. 11/184, 557 titled "Method of and Apparatus for Controlling Medical Navigation Systems") to less than a predetermined minimum value.

Accordingly, at least one method of mapping the surface of an anatomical structure in a subjects' body is provided using a remote medical navigation system to automatically navigate a medical mapping device in accordance with a routine over the surface of the anatomical structure. The method provides for localizing the device at a plurality of different locations on the surface, to create a map of at least portions of the anatomical surface. The method selects a routine for remotely navigating the medical device to the different locations on the surface based upon the location or topographical region of the anatomical surface being mapped. The user may input information identifying the location of the portion of the anatomical surface being mapped, or select a location from a menu of possible locations. Alternatively, the location of the portion of the anatomical surface being mapped may be automatically determined by localizing the medical mapping device and selecting a routine based upon which region of the heart the medical device is presently located. Likewise, the routine for automatically navigating or moving the medical device may be selected or automatically changed when the medical device is moved to a location or region that utilizes a different corresponding routine. The user may therefore select from a plurality of routines corresponding to different locations of the anatomical surface of the subject, such as the heart surface, where a routine may be selected to establish a combination of movements corresponding to the location or region for moving the medical device in a distinct pattern across the anatomical surface region.

Devices that can be used to map the vasculature in accordance with the methods of the preferred embodiment include various types of remotely actuated catheters. In the case of a remote magnetic navigation system, the catheters are magnetic catheters with magnetically responsive elements incorporated in the distal portion of the catheter. These devices can include, in addition to means that permit remote actuation, a connector on the proximal end with electrodes for connection to a recording system, a proximal shaft and a distal tip with a plurality of pace/sense electrodes located on the tip and shaft for the mapping of the vasculature.

Operation

In operation, a device such as a catheter is navigated through the vasculature and into the chamber of the heart. The catheter is navigated to a first location in the surface of the heart. The navigation system orients the distal end of the device and advances the medical device within a subject's body near to at least one known anatomical feature of the heart. The navigation system then initiates a touch sensitive movement to establish contact with the surface of the heart, and subsequently moves the medical device across the heart surface towards a ridge of the heart until a loss of contact is detected. From the point at which a loss of contact occurs, the navigation system is able to identify at least one point along the ridge of a subject's heart. The navigation system may repeat the movement to identify additional points along the ridge of the subject's heart, for identifying a three-dimensional location for the ridge line. The location of the ridge together with other regions of the chamber of interest derived from the mapping process describe earlier yields a good spatial representation for the user. Targets for further refining the map or for therapy delivery/RF ablation can be identified with the help of the anatomical map. Additionally, when desired, using the one or more identified points along the ridge, a pre-operative image of a portion of the heart including the corresponding ridge may be suitably registered to the identified three-dimensional location of ridge on the subject's heart.

One advantage of using a remote navigation system for determination of electrical mapping and ablation site(s) is that such a system can accurately return to a previously visited position for further data collection or checks. In the context of a magnetic navigation system, as described in U.S. Patent Application Ser. No. 60/583,855, filed Jun. 29, 2004, Localization of Remotely Navigable Medical Device Using Control variable and Length, incorporated herein by reference, the magnetic field vector and the length of device advancement from a known reference position/length can be repeatedly applied as control variables to yield reproducible return to a desired device tip position. As taught in the above U.S. patent application, the magnetic field vector and catheter length can be stored in the magnetic navigation system when the catheter tip is at a specific location, thereby serving to uniquely identify that spatial location. In this manner, after several sites have been explored, the recorded variables or a cost function associated with the various sites can be stored, and the device can be easily re-navigated to the site that yielded the best results. A fresh comparison of different sites can also be performed easily in this manner. This re-navigation can either be automatically performed by the remote navigation system under computer control, or driven by the user by manual control of the remote navigation system.

It is worth noting that while some of the examples above are in the context of a remote magnetic navigation system, the actuation method actually used by the remote navigation system could take various forms and is not constrained in any manner. For example, other remote navigation methods could employ mechanical pull wires controlled by servo motors, electrostrictive actuation, hydraulic actuation, and such other actuation schemes known to those skilled in the art.

Likewise, the techniques actually used in the methods detailed above could use varying levels of automation, from fully manual control to semi-automated control to fully automated control of the device steering and data recording elements.

What is claimed is:

1. A method for locating at least one point on an endocardial ridge of a subject's heart with a medical device actuated by a remote navigation system, the method comprising:
   advancing a medical device within a subject's body near to a known anatomical feature of the heart with the remote navigation system;
   establishing contact by the medical device with the surface of the heart;
   moving the medical device along the surface of the heart towards the anatomical feature until a loss of contact with the surface is sensed;
   detecting when a loss of contact with the heart surface has occurred; and
   determining the point where the loss of contact occurred to identify at least one point along the known anatomical feature.

2. A method for locating at least one point on an endocardial ridge of a subject's head with a medical device actuated by a remote navigation system, the method comprising:
   advancing a medical device within a subject's body near to a known anatomical feature of the heart with the remote navigation system;
   establishing contact by the medical device with the surface of the heart;
   moving the medical device along the surface of the heart towards the anatomical feature until a loss of contact with the surface is sensed; and
   determining the point where the loss of contact occurred to identify at least one point along the known anatomical feature, wherein the sensing of a loss of contact comprises detecting a change in tip orientation of more than a predetermined angle.

3. The method of claim 1 wherein the sensing of a loss of contact comprises detecting a change in orientation of the tip of the medical device that is more than a predetermined percentage from a previous tip orientation, measured relative to a reference orientation.

4. A method for locating at least one point on an endocardial ridge of a subject's heart with a medical device actuated by a remote navigation system, the method comprising:
   advancing a medical device within a subject's body near to a known anatomical feature of the heart with the remote navigation system;

establishing contact by the medical device with the surface of the heart;

moving the medical device along the surface of the heart towards the anatomical feature until a loss of contact with the surface is sensed; and determining the point where the loss of contact occurred to identify at least one point along the known anatomical feature, wherein the sensing of a loss of contact comprises identifying the existence of continuous contact by detecting an angular change in tip orientation of less than a predetermined amount, and determining when contact is no longer continuous.

5. The method of claim 1 wherein the at least one identified point along a ridge of a subject's heart is known with respect to an X-ray image of the subject's heart, and the corresponding ridge on a pre-operative image of the subject's heart is registered to the X-ray image using the at least one identified point along the ridge of the subject's heart.

6. A method for locating at least one point on an endocardial ridge of a subject's heart with a medical device actuated by a remote navigation system, the method comprising:

advancing a medical device within a subject's body near to a known anatomical feature of the heart with the remote navigation system;

establishing contact by the medical device with the surface of the heart;

moving the medical device along the surface of the heart towards the anatomical feature until a loss of contact with the surface is sensed; and determining the point where the loss of contact occurred to identify at least one point along the known anatomical feature, where the sequence of steps is automatically executed by the remote navigation system.

7. A method for locating at least one point on an endocardial ridge of a subject's heart with a medical device actuated by a remote navigation system, the method comprising:

advancing a medical device within a subject's body near to a known anatomical feature of the heart with the remote navigation system;

establishing contact by the medical device with the surface of the heart;

moving the medical device along the surface of the heart towards the anatomical feature until a loss of contact with the surface is sensed; and determining the point where the loss of contact occurred to identify at least one point along the known anatomical feature, where the remote navigation system is a magnetic navigation system.

8. The method of claim 1, where the remote navigation system is a mechanically actuate navigation system.

9. The method of claim 1, wherein the steps are repeated to identify a multiplicity of points to define the location of the ridge along a subject's heart.

10. A method for locating at least one point on a ridge of a subject's heart for anatomical mapping with a device actuated by a magnetic navigation system, the method comprising:

advancing a medical device within a subject's body to the point near the surface of the subject's heart;

applying a magnetic field to at least one magnetically responsive element in the tip of the medical device to cause the tip to deflect towards an interior heart wall of a subject's body and establish contact with an endocardial surface of the heart;

retracting the medical device while the tip is deflected against the surface of the heart; and detecting a variable change indicative of a loss of contact between the tip and heart surface along the ridge, and determining the location of the tip at the point where a loss of contact occurred.

11. The method of claim 10 wherein detecting a variable change comprises detecting a change in tip orientation of more than a predetermined angle.

12. The method of claim 10 wherein detecting a variable change comprises continually measuring the orientation of the tip of the medical device and determining the occurrence of a change in orientation of the tip of the medical device from a previously measured orientation by more than a predetermined percentage, measured relative to a reference orientation.

13. The method of claim 10 wherein detecting a variable change comprises detecting a decrease in contact force to a value less than a predetermined threshold value.

14. The method of claim 10 wherein the at least one identified point along a ridge of a subject's heart is known with respect to an X-ray image of the subject's heart, and the corresponding ridge on a pre-operative image of the subject's heart is registered to the X-ray image using the at least one identified point along the ridge of the subject's heart.

15. The method of claim 10, where the sequence of steps is automatically executed by the magnetic navigation system.

16. The method of claim 10, wherein the steps are repeated to identify a multiplicity of points to define the location of the ridge along a subject's heart.

17. A method for locating at least one point on a ridge of a subject's heart utilizing a magnetic navigation system, the method comprising:

changing the direction of a magnetic field applied by the magnetic navigational system to cause a catheter tip to be deflected until the tip establishes contact with the surface of the heart at a given distance from the ridge of a subject's heart;

identifying a direction of movement to provide a continuous line of contact along the heart tissue surface towards the ridge;

moving the catheter along the identified direction of movement towards the ridge until further movement is obstructed by the ridge;

retracting the catheter until a loss of tip contact with the tissue surface is sensed, and determining the location of the point at which the tip loses contact with the tissue surface.

18. The method of claim 17 wherein the sensing of a loss of contact comprises detecting a change in tip orientation of more than a predetermined angle.

19. The method of claim 17 wherein the sensing of a loss of contact comprises detecting a change in orientation of the tip of the medical device that is more than a predetermined percentage from a previous tip orientation, measured relative to a reference orientation.

20. The method of claim 17 wherein the sensing of a loss of contact comprises detecting a change in tip orientation of less than a predetermined angular amount.

21. The method of claim 17 wherein the sensing of a loss of contact comprises detecting a decrease in contact force to a value less than a predetermined minimum value.

22. The method of claim 17 wherein the at least one identified point along the ridge of a subject's heart is known with respect to an X-ray image of the subject's heart, and a corresponding ridge on a pre-operative image of the subject's heart is registered to the X-ray image using the at least one identified point along the ridge of the subject's heart.

23. The method of claim 17, wherein the steps are repeated to identify a multiplicity of points to define the location of the ridge along a subject's head.

24. The method of claim 17, where the sequence of steps is automatically executed by the magnetic navigation system.

* * * * *